United States Patent [19]
Markov

[11] Patent Number: 5,858,985
[45] Date of Patent: Jan. 12, 1999

[54] TREATMENT OF ASTHMA WITH FRUCTOSE-1,6-DIPHOSPHATE

[76] Inventor: Angel K. Markov, 5973 Hanging Moss Rd., Jackson, Miss. 39206

[21] Appl. No.: 943,438

[22] Filed: Oct. 3, 1997

[51] Int. Cl.[6] ............................. A61K 31/70; C07H 11/04
[52] U.S. Cl. ............................. 514/25; 514/826; 514/23; 536/117
[58] Field of Search ............................. 514/23, 25, 826; 536/117

[56] References Cited

U.S. PATENT DOCUMENTS

| | | | |
|---|---|---|---|
| 4,546,095 | 10/1985 | Markov | 514/23 |
| 4,703,040 | 10/1987 | Markov | 536/117 |
| 4,757,052 | 7/1988 | Markov | 514/23 |
| 5,731,291 | 3/1998 | Sullivan et al. | 514/23 |

Primary Examiner—John Kight
Assistant Examiner—Everett White

Attorney, Agent, or Firm—Patrick D. Kelly

[57] ABSTRACT

Fructose-1,6-diphosphate (FDP), a sugar-phosphate compound, can be useful in treating asthma, when administered as an inhalable drug, either by itself or as a component of a mixed formulation. On a cellular level, inhalable FDP appears to offer at least four beneficial effects for asthma sufferers: (1) it reduces histamine release by activated mast cells; (2) it suppresses production of oxygen free radicals by polymorphonuclear cells; (3) it helps suppress the activation and proliferation of T-lymphocytes; and, (4) it helps reduce the expression of interleukin compounds by T-lymphocytes. All four effects have been measured and shown to occur in animal and/or human tests, and these effects render FDP likely to help reduce and retard the progressive worsening of asthma that occurs in many sufferers. In addition, when tested in inhalable form on humans, FDP was shown to increase bronchial flow rates. All of these effects are beneficial, and can help asthma patients treated with FDP use asthma-control drugs which impose less stress on the user than more potent, aggressive asthma-control drugs.

11 Claims, 2 Drawing Sheets

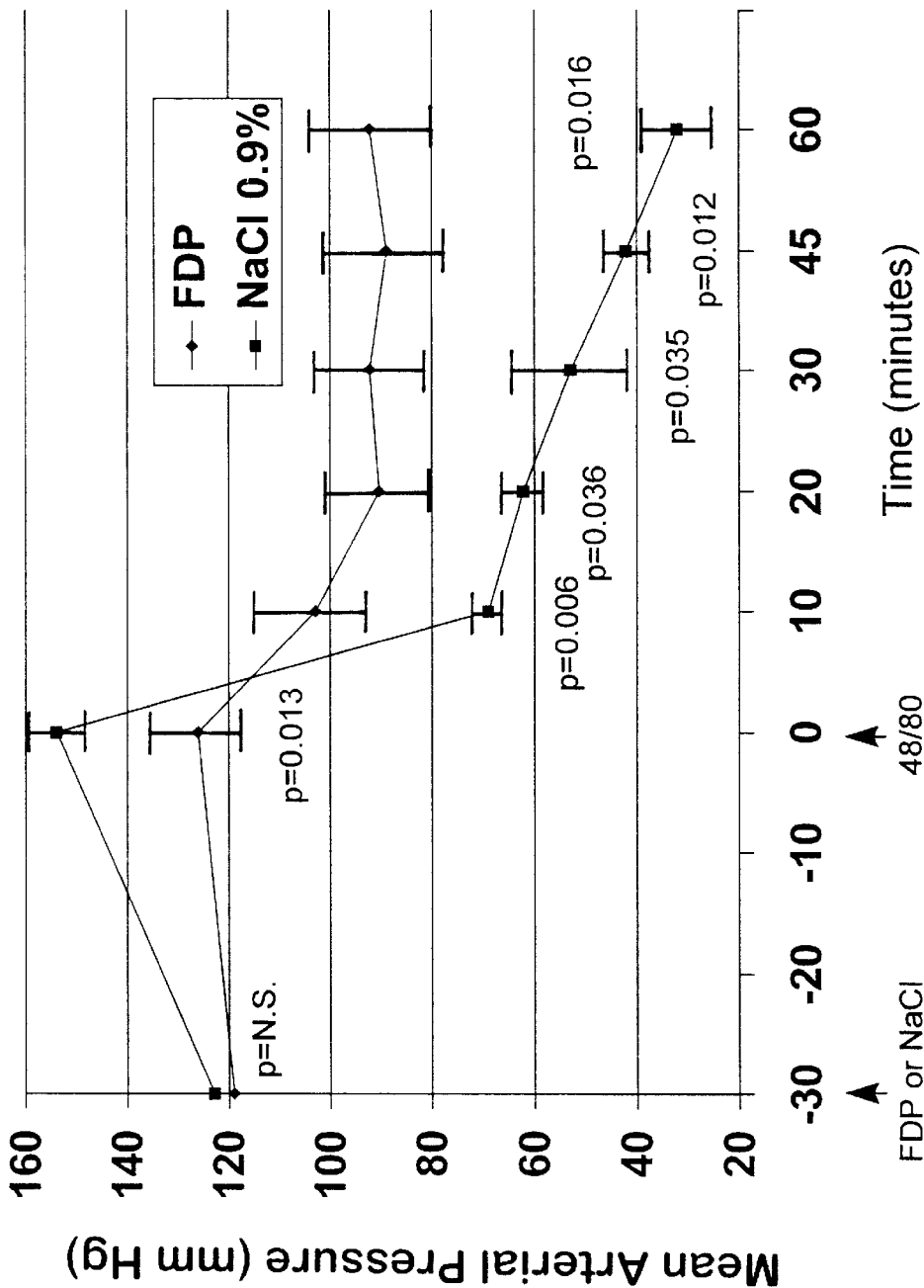

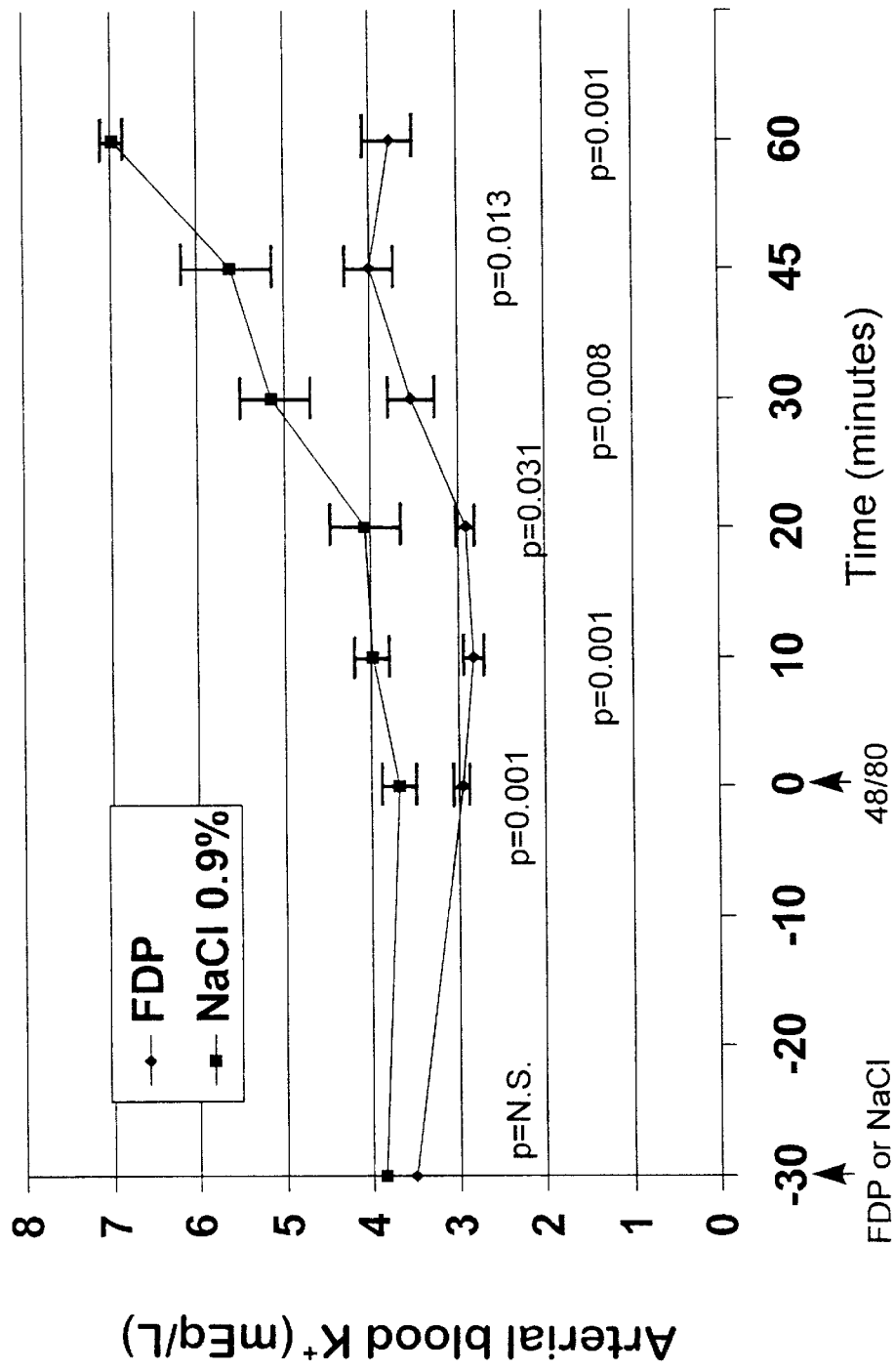

TREATMENT OF ASTHMA WITH FRUCTOSE-1,6-DIPHOSPHATE

BACKGROUND OF THE INVENTION

This invention relates to pharmacology, and to medical treatments for bronchial asthma.

Bronchial asthma is a common disease that involves narrowing of the airways, in a manner which renders it difficult for a person to breathe. As used herein, all references to "asthma" refer to bronchial asthma, which is distinct from a different problem known to physicians as cardiac asthma.

Asthma is a widespread problem (estimated to affect up to 10 to 20% of the population, at varying levels of severity), and a huge amount of information is available in the scientific and medical literature and in the popular press, on the physiological and cellular events and mediators that are involved in asthma, and on drug treatments that have been studied in an effort to help control it. A partial listing of review articles published just in the first half of 1997 include Everard 1997, Floreani et al 1997, Nourshargh 1997, Higgs 1997, Saint-Remy 1997, Bentley et al 1997, Jacoby 1997, Spector 1997, Corrigan et al 1997, and Barnes et al 1997 (complete citations to books and articles are provided below, immediately before the claims). The following is a very brief overview of certain relevant interactions that contribute to asthma attacks; more information can be obtained from any of the above cited articles, and numerous other such articles.

In asthma sufferers, narrowing of the airways is caused by an inflammatory reaction within the bronchial walls, involving various types of blood cells (including mast cells, eosinophils, and lymphocytes), muscle cells and other connective tissue cells, mediators, and cytokines. Typically, various allergens derived from organic material (such as pollen, house dust, feathers, animal hair, fungal spores, etc.) enter the bronchi, carried by the air that a person breathes in. These allergens stimulate formation of antibodies, mainly of the IgE class.

On subsequent exposure to the allergen, allergen-antibody interactions trigger a sequence of events which cause various cells (such as mast cells) in the bronchial walls to release mediators such as histamine (in general, "mediators" are pharmacologically-active molecules which are released by one or more types of cells, and which react with receptors on the surfaces of other types of cells, causing the receptor-bearing cells to initiate one or more responses). The intercellular mediators interact with cells such as bronchial smooth muscle cells, causing various cellular reactions that lead to bronchial constriction.

The histamine-mediated interaction between mast cells and bronchial smooth muscle cells is only one of the contributing mechanisms involved in asthma, and other types of cells and mediators are also involved in various chronic aspects of asthma. For example, the late phase of the asthmatic response is associated with an increase of non-specific bronchial responsiveness, and with infiltration and accumulation of neutrophils, eosinophils, and other leukocytes in bronchial tissue. In particular, eosinophils that become involved in the asthmatic inflammatory process are believed to release certain types of toxic mediators which can injure the bronchial epithelium, causing further inflammation.

In asthmatic attacks, eosinophil proliferation is believed to be largely controlled (or at least aggravated) by cytokines IL-3 and IL-5, which are produced and released by certain types of activated T-lymphocytes. Therefore, there has been considerable interest in the role of T-lymphocytes in asthma attacks, because they have been implicated in the regulation of IgE production.

In animal studies, after exposure to asthma-producing allergens and to various drugs that are used to simulate asthma in animals, activated T-cells have been identified by an increased expression of IL-2 receptors on the T-cell surfaces, and by increased production and release of the interleukin mediators IL-3, IL-4, and IL-5. Further evidence supporting the importance of the eosinophils and T-cells in the pathogenesis of asthma comes from histological studies performed before and after treatment with inhalable anti-inflammatory steroids. Following several weeks of treatment with inhaled steroids such as beclomethasone dipropionate, significant reductions in the number of eosinophils and activated T-cells in the airways of asthmatic patients have been observed.

Additional evidence which casts light on the role of T-lymphocytes in asthma is provided in articles such as Alexander et al 1992, Calderon et al 1992, Fukuda et al 1995, and Corrigan et al 1996, all of which discuss the ability of cyclosporine A to reduce asthmatic symptoms. Cyclosporine A is a highly specific inhibitor which reduces the activation and proliferation of T-type lymphocyte cells, which play a major role in the immune system; it is the compound that is administered to recipients of transplanted organs, to prevent their bodies from rejecting the foreign tissue. Alexander et al conducted a 6-month double blind placebo-controlled trial of cyclosporine A, which demonstrated a clear beneficial effect on spirometric measures in patients with chronic severe asthma.

In Fukuda et al 1995, patients with corticosteroid-dependent chronic severe asthma were treated with cylosporin A (5 mg/kg/day initially) for 12 weeks. This treatment significantly increased the peak expiratory flow, and it reduced the airway's hyper-responsiveness to acetyl-choline challenge. Fukuda and coworkers observed a significant reduction in T-lymphocytes bearing Il-2 receptors (a marker of T-cell activation) in the peripheral blood of these patients during the treatment.

Since cyclosporine is a highly selective and suppresses only T-type lymphocyte cells, these findings indicated that inhibition of T-lymphocytes activation in asthmatic patients, by cyclosporin A, reduced hyper-responsiveness of the airways, thereby improving expiratory air flow. However, these results are not especially promising or practicable for most asthma patients, since cyclosporin is a potent immunosuppressive compound that severely reduces a person's ability to resist infections. In general, cyclosporin is only administered to people who are facing life-threatening situations (such as recipients of transplanted organs, who will quickly die if their body rejects the foreign organ). It is not a medication that can be used frequently and safely by asthma sufferers.

One of the important features of asthma is that in many patients, it grows progressively worse, over the course of years. This arises from the fact that asthma involves allergic reactions that trigger the patient's immune system. As is well known, the immune system generally escalates its responses when it repeatedly encounters the same allergen, time after time. In asthma sufferers, the same allergens (such as pollen, house dust, feathers, animal hair, fungal spores, etc.) which provoked an initial attack are encountered again, and again, and again, because these types of allergens are so endemic, widespread, and unavoidable.

Therefore, many asthma sufferers are forced to gradually escalate their treatment regimens. Typically, when most patients suffer a first asthma attack that requires medical treatment, they try out one or more relatively mild, unaggressive drugs, in the hope that such drugs can provide adequate relief without imposing too much disruption or stress on the fragile tissues inside the lungs. Even if such relatively mild drugs give adequate relief for a period of months or years, a large fraction of the population of asthma sufferers suffer from increasingly severe attacks, as their immune systems become more and more hyper-sensitized to one or more types of allergens. Such patients must subsequently escalate their treatment regimens, and must begin using other drugs that are more potent, aggressive, and harsh, and which inflict higher levels of disruption and stress on the various types of immune cells and lung tissues involved in asthma attacks.

Despite the enormous amount of research on asthma and on drugs to help control asthma attacks in sufferers, there is no adequate and satisfactory treatment for asthma. Most sufferers must struggle with a variety of drugs, none of which are completely effective, and if their symptoms gradually grow worse (as often happens), they must periodically escalate their treatments to more powerful drugs, which inflict progressively greater demands, stress, and damage on their lungs.

Accordingly, one object of this invention is to disclose that a pharmacological agent which has not been recognized previously as an asthma treatment is, in fact, a useful and effective treatment for asthma attacks.

Another object of this invention is to disclose that fructose-1,6-diphosphate, a sugar-phosphate compound which is present in all living cells, can be a harmless and highly useful component of asthma therapy, with the potential for both (1) helping to treat asthma attacks, and (2) helping to reduce and prevent the gradual worsening of asthma attacks that occur in many sufferers, thereby allowing those patients to continue using, for as long as possible, asthma-control drugs that are relatively mild and benign, rather than the harsher and more potent drugs that would be required if their asthma attacks grow more severe over the course of months or years.

Another object of this invention is to disclose that fructose-1,6-diphosphate can be included as a component in various types of inhalable drug treatments for asthma sufferers, or as a stand-alone inhalable treatment for asthma sufferers.

These and other objects of the invention will become more apparent through the following summary, description, and examples.

SUMMARY OF THE INVENTION

Fructose-1,6-diphosphate (FDP), a sugar-phosphate compound which is an intermediate that is generated and quickly consumed in the process of glycolysis, can be useful in treating asthma. FDP can be included as a component in inhalable drug treatments; it can also be formulated as a stand-alone inhalable treatment. When administered in inhalable form, FDP can help treat asthma attacks by reducing bronchial constriction and increasing bronchial flow rates. It is also likely to help reduce and retard the progressive worsening of asthma that occurs in many sufferers. Both effects are beneficial, and can help asthma patients use asthma-control drugs that are relatively mild and benign, and which impose less stress on the user than more potent and aggressive drugs. When inhaled into the lungs, FDP appears to have at least four beneficial effects: (1) it reduces histamine release by activated mast cells; (2) it suppresses production of oxygen free radicals by polymorphonuclear cells; (3) it helps suppress the activation and proliferation of T-lymphocytes; and, (4) it helps reduce the expression of interleukin compounds by T-lymphocytes. All four effects have been measured and shown to occur in animal and/or human tests, and all four are beneficial. Accordingly, FDP in inhalant form can help reduce and control the severity of asthma attacks, and it can help reduce or retard the tendency of asthma to grow progressively worse in many sufferers.

BRIEF DESCRIPTION OF THE DRAWINGS

FIG. 1 is a graph showing that FDP treatment helped sustain blood pressure in animals injected with compound 48/80, a test drug that can induce shock and death in lab animals by causing high levels of histamine release.

FIG. 2 is a graph showing that FDP treatment helped reduce unwanted elevations in blood plasma levels, in animals injected with compound 48/80.

DESCRIPTION OF THE PREFERRED EMBODIMENTS

This invention uses fructose-1,6-diphosphate (FDP), a naturally occurring sugar-phosphate compound in which phosphate groups are bonded to the #1 and #6 carbon atoms of a fructose molecule. Some scientists refer to FDP as fructose-1,6-biphosphate, or fructose-1,6-bisphosphate.

The 1,6-isomer of fructose diphosphate is the only isomer of interest herein. Other isomers (such as fructose-2,6-diphosphate) exist in nature, but they are not relevant herein, and they are excluded from any references herein to FDP or fructose diphosphate.

Inside cells, fructose-1,6-diphosphate is created and then quickly consumed as an intermediate in the series of reactions that make up glycolysis. Glycolysis is a fundamental biological process in which cells use a series of enzymatic steps to break apart glucose, a 6-carbon sugar molecule, to generate energy. Glycolysis is discussed in detail in nearly any textbook on biochemistry, physiology, or cell biology; see, e.g., any edition of Stryer's or Lehninger's *Biochemistry,* Guyton's *Medical Physiology,* or Alberts et al, *Molecular Biology of the Cell.* As a short-lived intermediate that is created and then quickly consumed, FDP normally is present in cells only at relatively low concentrations.

It should be noted that a large number of potential medical uses have been proposed for FDP; for example, it has been proposed and studied as a treatment for heart attack and stroke victims, as a preservative agent for organs that are being transplanted, and as an additive for blood cells that are being frozen and stored. US patents which contain such proposals include U.S. Pat. Nos. 4,546,095 (Markov 1985), 4,703,040 (Markov 1987), and 4,757,052 (Markov 1988). Scientific articles that contain similar proposals or study data include Markov et al 1980, 1986, and 1987, Brunswick et al 1982, Marchionni et al 1985, Granot et al 1985, Farias et al 1986 and 1989, Grandi et al 1988, Zhang et al 1988, Cacioli et al 1988, and numerous other articles.

However, despite all of these published articles and patents, which stretch back at least to 1980, a high degree of skepticism and reluctance still exists regarding FDP use to treat ischemia or hypoxia, due to a number of factors such as:

(1) assumptions that FDP, a diphosphate with a strong negative charge, probably cannot enter cells in sufficient quantities to have significant effects on the intra-cellular metabolism;

(2) assumptions that FDP has a very short half-life in the blood, and will effectively disappear from the blood within a few minutes after injection or infusion;

(3) fears that administration of FDP to oxygen-starved cells would lead to substantial increases in lactic acid levels. This could be very harmful, since excess lactic acid can poison an enzyme called phosphofructokinase (PFK), which is the crucial rate-regulating enzyme in glycolysis;

(4) reports which state that FDP had no beneficial effects, in various studies. Examples of these negative articles include Eddy et al 1981, Pasque et al 1984, Tortosa et al 1993, and Angelos et al 1993;

(5) the high level of difficulty in handling and storing, for any length of time, a compound that will readily and spontaneously hydrolyze, losing one of its phosphate groups to form fructose monophosphate, which is useless.

For these and other reasons, despite all of the numerous proposals that FDP might somehow be useful in medicine, FDP simply is not being used or prescribed by any practicing physicians, for any medical conditions. The only known exceptions are (1) a few small and limited clinical trials, at research centers; and (2) very limited use in a few countries (such as China) of semi-sterile preparations that cannot meet the government approval requirements for human drugs in the United States and most other industrialized nations.

The foregoing is general information on FDP. It should be noted and emphasized that, to the best of the Applicant's knowledge and belief, no prior articles or publications have ever taught or even suggested that FDP would be a useful treatment for asthma. The discovery of that new utility is, to the best of the Applicant's knowledge and belief, entirely new and original. Its potential for use in treating asthma was not even suspected by the Inventor until recently, even though the Inventor (a cardiologist) has been working with FDP, for other medical uses, for almost 20 years.

The Examples below describe several different types of tests, all of which support and help confirm the belief that FDP, when administered in inhalant form directly into the lungs of an asthma sufferer, is highly useful for treating asthma attacks. These tests are briefly summarized in the following paragraphs, and detailed protocols and results are provided in the examples, tables, and figures.

Example 1 describes a set of tests the release of histamine by "mast cells", which are a certain type of white blood cells. Histamine release by mast cells plays a major role in a variety of inflammatory, edematous, and anaphylactic shock reactions, and histamine has been shown to play a contributory and aggravating role in asthma attacks.

Microvascular leakage is also an important feature of asthma, and may be triggered by various inflammatory mediators. If excess histamine is released in or around the lungs, it can cause edema, plasma exudation into the airways, and release of kinins and complement fragments that can inhibit membrane-bonded $Na^+$—$K^+$ ATPase; histamine has been shown to inhibit $Na^+$—$K^+$ ATPase, in gastric mucosa, to the same degree as ouabain. By contrast, FDP has been shown to help restore the activity of $Na^+$—$K^+$ ATPase in vitro, in cardiac tissue, by the same inventor herein, in tests which showed that FDP can help reduce the toxicity levels of oleander extracts.

Accordingly, FDP was tested to determine whether it could help reduce histamine release, under in vivo conditions. These tests used a substance known as compound 48/80, which powerfully provokes the release of histamine, in test animals. In animals such as rats, if a controlled quantity of compound 48/80 is injected, the animal will die fairly quickly, due to various organ impairments that result from massive edema and anaphylactic shock.

As described in Example 1, and as shown by the data in FIG. 1, FDP was shown to be highly effective in protecting animals against the damaging effects of compound 48/80. The system hemodynamics (such as arterial blood pressures, and partial pressure of oxygen ($PO_2$) values) were significantly better in the FDP-treated group than in the saline-treated control group. In rats injected with compound 48/80 and treated with saline, a significant increase in plasma $K^+$ was observed, indicating disruptions of the $Na^+$—$K^+$ ATPase system; by contrast, plasma potassium levels in the FDP-treated group were much closer to normal levels, indicating effective protection of that system by the FDP. Mortality rates were greatly reduced by FDP treatment; the control group had a 100% mortality rate, while the FDP-treated group had only 20% mortality. All of these results, in Example 1, strongly indicate that FDP is effective in reducing histamine release in treated animals. This is a potentially very beneficial effect, in asthma sufferers.

Example 2 presents two different sets of tests, both of which show that FDP can help protect the functioning of a certain class of enzymes known as membrane-bound $Na^+K^+$ ATPase enzymes, which are very important in certain aspects of cell metabolism. One set of cell culture tests used a type of toxic glycoside isolated from oleander plants, which are poisonous. These toxic glycosides can shut down the membrane-bound $Na^+K^+$ ATPase enzyme system, and it was shown that FDP can protect that enzyme system from being shut down by those toxins.

Example 2 also describes in vivo tests which showed that when compound 48/80 was administered to intact animals, it caused a large increase in potassium ($K^+$) levels in the blood plasma. This effect is caused by disruption of membrane-bound $Na^+K^+$ ATPase enzymes, since those enzymes normally perform the function of pumping potassium ions into cells, thereby reducing the concentrations found in extracellular fluid. It was shown, in the in vivo tests, that FDP can substantially reduce that effect of compound 48/80. This adds more evidence showing that FDP can help protect an important enzyme system from disruption. This is an important protective activity, since disruption of that enzyme system appears to be a significant aggravating feature in asthma attacks.

Examples 3 and 4 describe tests which showed that FDP can also help reduce the unwanted activation of T-type lymphocytes (also referred to as T-cells). T-cell activation generally refers to (1) proliferation of T-cells in an affected tissue area, and (2) release of certain intercellular mediators, called cytokines, which act as hormones that interact with other cell types.

In biopsies from asthmatic patients, lymphocyte content is usually slightly increased (compared to non-asthmatics). A potentially more important difference is that the T-lymphocytes in asthmatics are usually more highly activated, as shown by expression of Interleukin-2 (IL-2) receptors on the surfaces of the T-cells. Analysis of cytokines in concentrated broncho-alveolar lavage (BAL) obtained from asthmatic patients also reportedly demonstrate significant increases in various interleukines (IL-5, IL-2, IL-1, IL-6, IL-8; see Virchow et al 1995). Those results suggest that the number of eosinophil cells and activated T-cells play an important role in asthma.

It is believed that certain types of cytokines (such as IL-5 and IL-2) released by T-cells react with receptors on the surfaces of other cells in the lungs, such as bronchial smooth muscle cells. These reactions trigger various cellular reactions which lead to constriction of the bronchial airways.

Accordingly, it is believed that treatment agents which can help reduce (1) the proliferation of T-cells in an affected region, and (2) the release of IL-2, IL-5, and other unwanted cytokines by T-cells in the lungs, can be a useful treatment for asthma sufferers. This is supported by test results showing that treatment with cyclosporin A can induce significant improvement in pulmonary function tests, in patients suffering from asthma (e.g., Alexander et al 1992; Fuguta et al 1995). However, cyclosporine treatment is not a promising treatment for most asthma sufferers because of its side effects, including organ toxicity and a general suppression of the immune system.

Accordingly, if FDP, administered either in inhalant form directly into the lungs, or in injectable form such as by intravenous infusion, can suppress T-cell activation in the bronchia and lungs without causing the unwanted complications and side effects caused by cyclosporine A, it would be greatly preferable to cyclosporine, as a treatment for asthma. The results described above indicate that it can, and that it offers a highly promising and useful agent for treating asthma.

The ability of a compound such as FDP to help suppress T-cell activation is usually tested, in vitro, by stimulating T-cells with a mitogen compound known as concanavalin A (conA), and by testing potential treatment agents, to evaluate how well they can suppress the T-cells' response to the conA stimulation. When such tests were done using FDP, the results showed that FDP did indeed help to suppress both (1) the proliferation of T cells, as described in Example 3, and (2) the synthesis of cytokines by the T-cells, as described in Example 4.

Example 5 describes the ability of FDP to substantially reduce the severity of bronchial attacks in lab animals, which can be induced by having the animals inhale a compound called methacholine.

Example 6 describes the results of tests on human volunteers who do not suffer from asthma, showing that inhalation of FDP, in nebulized mist form, significantly increases bronchial and pulmonary capacity. When compared to baseline values, inhalation of nebulized FDP for 5 consecutive breaths caused a substantial increase in "peak expiratory flow rate" (PEFR), which measures how rapidly someone can blow air out of his or her lungs, through the bronchial passageways.

Example 7 further indicates that in one of the test subjects who participated in the PEFR tests, and who was suffering from a chronic cough, apparently due to allergic bronchitis, repeated inhalation of FDP over a period of 10 days led to a substantial improvement in the bronchitis, and to essentially complete resolution of the coughing problem. Accordingly, although more testing will be required to fully evaluate these possibilities, it is believed that inhalable forms of FDP are likely to offer useful treatments, in at least some patients, for bronchitis, chronic coughing, and possibly other chronic pulmonary problems as well, such as emphysema.

Formulations and Dosages

The main preferred method for using FDP to treat asthma involves inhalation of the FDP, in the form of an aerosol, so that the FDP should come in direct contact with mast cells and T-cells in the bronchial mucosa. Such aerosol or nebulized formulations can use liquid carrier solutions if desired, made by methods such as dissolving FDP in a suitable aqueous carrier, such as a normal saline solution.

If inhalable forms of FDP are used, dosages should generally be in the range of about 2 to about 100 mg/breath, in nebulized form, depending on the age and size of the patient, the severity of the attack, and other such factors. Like most sugar compounds, FDP is highly soluble in water, and aqueous solutions containing nearly any desired concentration of FDP can be provided. Preferred upper concentrations for inhalers will usually reflect an effort to balance two competing factors against each other: (1) a desire to package a substantial quantity of FDP in a small container, and (2) the need to avoid tissue irritation, which may be encountered as concentrations are increased. In general, it is anticipated that aqueous solutions containing about 5% to about 40% (w/v) FDP are suitable, and that solutions containing about 10% to about 30% are likely to be preferred.

As described in Example 6, healthy human volunteers were tested to evaluate the effect of inhaled FDP on "forced expiratory flow rate" (FEFP). These tests used a nebulizer connected to a bottle containing 10% (w/v) FDP in water. Each patient took 5 consecutive breaths from the nebulizer during these tests, and the total quantity of FDP inhaled by each patient averaged about 12 mg. One test subject, who inhaled higher dosages of FDP to evaluate possible side effects, inhaled 700 mg of the sodium salt of FDP using a 20% w/v solution; during a different test, the same volunteer inhaled 700 mg of sodium FDP, using a 10% w/v solution. Each such test involved a ten minute inhalation period. In both tests, no side effects were detected.

It may also be possible to provide an inhalable form of FDP, for treating asthma, in a lyophilized or partially lyophilized, powdered or microcrystalline form. Briefly, a method for partially lyophilizing FDP has been developed by Cypros Pharmaceutical Corporation of Carlsbad, Calif. (the assignee herein), wherein the preparation contains a moisture content of about 10% to about 25%, by weight. This is a surprisingly high moisture content, in view of the fact that most other lyophilized drug preparations are dried to a point where the residual water content is about 2% or less. This method and preparation is described in detail in U.S. Pat. No. 5,731,291, which has been examined and allowed, and which will issue in late 1997 or early 1998. The contents of that application are hereby incorporated by reference.

Various methods are known in the art for generating microcrystalline powders which are loaded into inhalation devices; for example, cakes or powders can be generated under sterile conditions, then ground into fine powders, and then loaded into inhaler cylinders, using clean-room facilities and procedures. Alternately or additionally, various anti-crystallizing compounds are known, and such compounds, as well as agitator particles or devices which can pulverize any agglomerations or oversized clumps into fine powders, can be packaged into an inhaler device along with the FDP. If desired, any or all of these methods can be adapted for use in creating dried FDP powders for inhalation by asthma sufferers, as described herein. In addition, this type of lyophilized FDP powder might also be added to a powdered or other dry preparation containing one or more other drugs for treating asthma. Any such dry preparation would need to be tested, to ensure that it does not irritate any tissue or cause other adverse effects.

If desired, FDP can also be intravenously injected, to treat severe attacks of asthma. This method of administration can have two distinct benefits: systemic FDP can help the entire body cope with the hypoxic stresses that are caused by the patient's inability to breathe in enough air, and any FDP which enters the lungs can help directly treat the various mechanisms that are aggravating the attack.

If injectable FDP is used, a solution such as about 5 to about 30% (weight per volume, w/v) FDP in aqueous solution (distilled water, normal saline solution, etc.) can be administered, in any of several ways. For example, to achieve a relatively high blood concentration fairly quickly, a slow intravenous bolus can be administered over 5 to 15 minutes, in a dosage range such as about 75 to about 350 mg/kg. Following this initial bolus, FDP can be administered via continuous infusion at a rate such as about 0.1 to about 1.0 mg/kg per minute, until the asthmatic crisis is resolved. Alternatively, a slow IV bolus can be given every few hours such as every 6 hours, at dosages such as suggested by the above.

It should also be noted that FDP, in either inhalable or injectable form, can be mixed, or otherwise administered in conjunction with, various other drugs that are useful for treating asthma. As one example, a liquid or crystalline preparation of FDP can be packaged in the same inhalant cylinder that contains a second asthma-treating drug; alternately, an asthma sufferer who is struggling with an attack may alternate FDP inhalation with inhalation of a second drug.

In general, oral administration of FDP is not likely to be effective, since the FDP will be substantially degraded by stomach acidity and other factors before it can enter the bloodstream.

Articles of Manufacture: Pre-packaged Inhalation Cylinders

This invention also discloses articles of manufacture comprising inhaler cylinders or other inhalation devices which have been loaded with FDP in a form and in a dosage or concentration that is ready for inhalation by an asthma sufferer. Preferably, such devices should include small inhaler cylinders that are small enough to fit into a conventional pocket or purse, so they can be carried anywhere by asthma sufferers with little or no inconvenience. Such devices might hold up, for example, about 50 to 100 grams (about 2 to 4 ounces) of material. In addition, such inhalation devices should also include larger cylinders, which preferably can be refilled when empty, comparable to the oxygen-containing cylinders that are often carried by emphysema sufferers, for use in homes, clinics, and other such locations. Such cylinders are conventionally made of aluminum, molded plastic or other suitable materials, and are manufactured with orifices that are suitable for accommodating inhaler nozzles which deliver a pre-determined dosage of material each time the nozzle is depressed or otherwise manipulated. Personal-use inhalers are usually sold with such nozzles already attached.

EXAMPLES

EXAMPLE 1: REDUCTION OF HISTAMINE RELEASE BY MAST CELLS

As noted above, the release of histamine by mast cells plays a significant role in aggravating asthma attacks. FDP was evaluated to determine whether it could help suppress histamine release by mast cells, in tests that use a compound called "48/80", which is known to trigger the release of histamine by mast cells. This compound, if injected into an animal at an appropriate dosage, will trigger sufficient histamine release to send the animal into anaphylactic shock, which poses a lethal challenge. Useful physiological measurements can be made during the test period, and if mortality is studied as an endpoint, an animal is deemed to survive if it lives for 48 hours after injection of the 48/80 compound.

Anesthetized male Sprague-Dawley rats (n=20) weighing 448±7.4 gm were randomly assigned into 2 groups. Animals in the FDP-treated group were injected intraperitoneally (IP) with a 10% (w/v) solution of FDP in water, at a dosage of 2.5 gm/kg (i.e., 2.5 grams of FDP per kilogram of body weight). Animals in the control group (n=10) were injected with comparable volumes of normal saline, at 25 ml/kg. Thirty minutes later, all rats were injected IP with compound 48/80, at 5 mg/kg.

During the test period, the arterial pressure in the FDP group was significantly higher than in the saline group (P<0.005) (FIG. 1). Plasma potassium in the FDP group was lower (P<0.01) (FIG. 2). The average arterial partial pressure of oxygen ($PO_2$) in the FDP group was 121±6.1 mm Hg and the saline group 98±9.2 mm Hg. Mortality in the saline (control) group was 100%; by contrast, mortality in the FDP-treated group was only 20% (P<0.001). The mean survival time for the rats treated with saline only (controls) was 32.7±6 min after injection with the 48/80 compound (time range: 20 to 70 min). Only two rats in the FDP group died (at 10 and 50 min).

In summary, death as a result of compound 48/80-induced shock appears to be due to hypotension, bronchospasm and negative inotropic effect caused by histamine. It is concluded that FDP is an effective mast cell inhibitor in vivo, and is effective in counteracting the mast cell histamine release induced by injection of compound 48/80.

EXAMPLE 2: PROTECTION OF $Na^+K^+$ ATPase ENZYMES

Various processes involved in asthma attacks can disrupt the proper functioning of membrane-bonded $Na^+$—$K^+$ ATPase enzymes, which are important in various aspects of cellular metabolism, including the ability of cells to sustain the proper concentration gradients of sodium and potassium ions across the cell membranes.

In a research project which was not initially related to asthma, the Applicant and his coworkers investigated the potential use FDP as an antidote against oleander poisoning. Oleanders are a well-known flowering shrub, widely used as a landscaping plant. Despite their widespread use, they are highly poisonous. A number of deaths have been attributed to it, usually involving the burning of oleander leaves and stems in cooking fires, or the use of oleander stems as spits on which meat was suspended while being roasted or barbecued.

The poisonous toxins in oleander plants involve certain types of glycosides which can severely disrupt various gastrointestinal and cardiac functions. One of their main modes of activity is disruption of membrane-bonded $Na^+$—$K^+$ ATPase enzymes. Accordingly, oleander toxins offer a model for testing the ability of candidate drugs to help protect $Na^+$—$K^+$ ATPase enzymes against attack and disruption by various toxins, and by other compounds which are involved in asthma attacks, such as histamine, certain types of kinins, and certain types of enzyme-disrupting complement fragments.

Oleander toxins were prepared by air-drying leaves from red-flowering Nerium oleander plants for 4 days, pulverizing the leaves to a fine powder in a blender, and extracting the leaves in a 95% ethyl alcohol solution for 10 days. After extraction, the tincture was filtered, and part of the alcohol solvent was removed by flash evaporation, to a volume where 1 gram of crude drug was equal to 1 ml of alcohol solution. The extract was stored as a stock solution at 0° C., and periodically analyzed for alkaloid content by high pressure liquid chromatography, using oleandrin as an external standard. To carry out the in vitro tests described below, 1 to 2 μL aliquots of the stock solution were used, containing 0.1 top 2 mg of the toxins. Ethanol, at the concentrations used, was also tested, and was shown to have no effect on membrane ATPase activity.

To prepare cardiac membrane fractions with membrane-bonded $Na^+$—$K^+$ ATPase enzymes, adult Sprague-Dawley rats, 250±25 g body weight, were anesthetized with ketamine HCl (50 mg/kg body weight) by intraperitoneal injection. Whole hearts were dissected, washed in saline, quickly frozen in liquid nitrogen, and stored at −80° C. until use.

When ready for use, intact isolated rat hearts were transferred to ice-cold homogenizing medium (50 mM $Na_2HPO_4$, 10 mM $Na_2EDTA$, and 25 mM NaF, pH 7.4). The ventricular sections of the hearts were dissected, and blood was removed by squeezing the ventricles on absorbing paper. The membrane vesicles were prepared as described by Jones et al 1979. Briefly, the minced tissue from each ventricle was homogenized in 10 ml of homogenizing medium using Polytron at a power setting of 7 with 3 bursts of 15 sec each. An additional 5 ml of medium was added and the homogenate was sedimented twice for 20 min at 14,000 g. The supernatant from the second spin was then centrifuged at 45,000 g for 30 min. The resulting pellet was suspended in 10 ml of homogenizing medium containing 0.6 ml NaCl (pH 7.0). This suspension was centrifuged again at 45,000 g for 30 min.

The pellet obtained after this centrifugation, consisting of crude membrane vesicles, was suspended in a storage buffer (30 mM histidine, 0.25 M sucrose, 10 mM EDTA, and 10 mM NaF, pH 7.5) and stored at −80° C. until use. Protein content was determined using a Biorad protein assay kit, with gamma globulin as a standard.

The $Na^+$—$K^+$ ATPase activity levels for these sarcolemmal membrane preparations was determined calorimetrically by measuring how much inorganic phosphate (Pi) was liberated when the ATPase enzyme hydrolyzed ATP to release phosphate groups. A 1 ml reaction mixture was used, and contained (in final concentration) 5 mM ATP, 5 mM magnesium chloride ($MgCl_2$), 100 mM NaCl, 20 mM KCl, 135 mM imidazole/HCl buffer (pH 7.5), and 50 g of enzyme protein. The total cationic ligand-stimulated ATPase activity was measured with $Na^+$, $K^+$ and $Mg^{++}$ present in the reaction mixture. $Mg^{++}$ ATPase activity was measured in the presence of 1 mM ouabain, a specific inhibitor of $Na^+$—$K^+$-ATPase. Thus, delineation of the ($Na^+$—$K^+$)-activated component of total ATPase was obtained by determining the difference between total ATPase activity, and $Mg^{++}$ ATPase activity. The incubation was carried out at 37° C. for 30 min and the reaction was stopped with trichloroacetic acid at a final concentration of 5%. Samples then were assayed for inorganic phosphate. Enzyme activity was expressed as micromoles of inorganic phosphate released from the ATP substrate, per milligram of enzyme protein, per hour.

The effects of oleander extract, in the absence of FDP (controls) or after pretreatment with 500 μM FDP, were assessed by preincubating the $Na^+$—$K^+$ ATPase enzyme preparations with various concentrations of oleander toxins for 5 minutes, then adding ATP to supply the necessary substrate for enzymatic hydrolysis which released phosphate groups.

The results, shown in Table 1, clearly show that FDP reduced disruption of the $Na^+$—$K^+$ ATPase enzyme system by the glycosidic toxins in oleander plants. All FDP treatment results are statistically significant at levels of more than 99%.

TABLE 1

PROTECTION OF $Na^+$—$K^+$ ATPase ENZYMES BY FDP

| Oleander extract | No FDP | With FDP |
|---|---|---|
| Control (0 mg) | 21.58 ± 4.40 | — |
| 0.1 mg | 18.04 ± 1.12 | — |
| 0.5 mg | 14.48 ± 0.52 | — |
| 1.0 mg | 9.35 ± 0.55 | 19.32 ± 0.62 |
| 2.0 mg | 4.85 ± 0.57 | 15.75 ± 0.39 |

FDP does not react with glycosidic toxins from oleanders. Instead, it acts by providing a useful energy substrate for cellular components. Accordingly, the oleander toxin test offers a valid model which indicates that FDP can help protect membrane-bound $Na^+$—$K^+$ ATPase enzymes against at least some types of disruption.

To further evaluate the effects of FDP on membrane-bound $Na^+$—$K^+$ ATPase enzymes, a set of in vivo tests were also carried out, using rats. In rats injected with compound 48/80 (described in Example 1) and not protected by FDP, potassium ion ($K^+$) levels in blood plasma substantially increased. This offers strong evidence that the $Na^+$—$K^+$ ATPase system is being disrupted, since that enzyme normally pump $K^+$ ions from extracellular fluids, into cells. By contrast, in rats treated with FDP, $K^+$ levels in blood plasma remained within normal values (P<0.01), despite identical treatment with compound 48/80.

Accordingly, both sets of observations (the oleander toxin test results, and the compound 48/80 test results), in combination, offer good evidence that FDP can help protect $Na^+$—$K^+$ ATPase system against disruption and inactivation. Since disruption of that enzyme system is an aggravating factor in asthma attacks, these results provide evidence of a specific cellular mechanism by which FDP can help treat and reduce the severity of asthma attacks.

EXAMPLE 3: INHIBITION OF T-CELL ACTIVATION AND PROLIFERATION

It has long been known that in patients with allergic asthma, exposure to relevant allergen(s) induces degranulation of mast cells in the bronchi; this mast cell degranulation leads to histamine release by the mast cells, and to subsequent bronchial constriction.

In recent years, biopsies on fluids or tissues obtained from the bronchial airways of asthma sufferers also show infiltration by eosinophils and mononuclear lymphocyte cells. In such biopsies from asthmatic patients, lymphocyte numbers are slightly increased. More importantly, when compared to control subjects, T-lymphocytes in asthmatic patients are much more highly activated, as shown by substantially higher numbers of certain types of interleukin receptor proteins (especially interleukin-2, abbreviated as IL-2) on the surfaces of the activated lymphocytes. In addition, analysis of cytokine concentrations in the fluids obtained by bronchio alveolar lavage (BAL) of asthmatic patients have demonstrated substantial increases of certain interleukines, including IL-1, IL-2, IL-5, IL-6, and IL-8. This has led researchers to conclude that the number of activated T-cells in bronchial tissues play an important role in allergic asthma (see, e.g., Virchow et al 1995).

Accordingly, FDP was tested to determine whether it could help suppress the activation of such T-type lymphocytes, i.e., to determine whether it could help reduce the number of interleukin receptors expressed by the cells. These tests used a mitogen compound called Concanavalin A (Con A), which is known to activate T-cells. For comparative purposes, FDP's ability to reduce T-cell activation in these tests was compared against cyclosporine, a powerful immunosuppressant drug which selectively suppresses T-cell activation.

Lymphocyte cells were isolated either from human venous blood or rat spleen. The cells were suspended in Dulbecco's media. A manual cell count was done using 0.1 ml of Trypan blue and 0.1 ml of the cell media mixture. The cell count was adjusted to $1 \times 10^6$ cells/ml and viability ranged between 92 to 98%. Tissue culture multi-well plates were used for incubation and in each well 0.1 ml of cell suspension was placed. To the FDP treatment wells (in triplicate) were added 0.1 ml of FDP from 10% stock solution, in serial dilutions which included 1:10, 1:100, 1:250, 1:500; 1:1000, and 1:10000). Cyclosporine treatment wells received 0.1 ml cyclosporine A, at various concentrations including 500 ng/ml, 50 ng/ml; 5 ng/ml and 0.5 ng/ml. All wells except control wells received concanavalin A (conA) at 10 pg (0.01 ml). The final volume for all wells was 0.21 ml.

After incubation, the cells were pulsed in 5% $Co_2$ at 37° C. with 1 $\mu$Ci of ($^3$H)-thymidine (i.e., the cells were incubated for a controlled period of time with thymidine, one of the building blocks of DNA, which contained tritium, a radioactive isotope of hydrogen). The cells were harvested, and washed to remove any tritiated thymidine that had not been incorporated into new DNA. The radioactivity levels of the treated cells were then measured, using a scintillation counter. The results, in Table 2, are reported as counts/min.

As shown in Table 2, lymphocytes which had been activated by ConA treatment synthesized high levels of new DNA. however, treatment by either FDP or cyclosporine was able to block ConA activation of the lymphocytes.

TABLE 2

INHIBITION OF RAT T-LYMPHOCYTE PROLIFERATION AFTER STIMULATION WITH CON-A, BY VARYING CONCENTRATIONS OF FDP

| Treatment | Activation Index |
| --- | --- |
| Controls (no Con-A or FDP) | 527 ± 139 |
| 10 $\mu$g Con-A; no FDP | 30718 ± 4316 |
| Con-A plus 1:10 FDP | 101 ± 16 |
| Con-A plus 1:100 FDP | 190 ± 42 |
| Con-A plus 1:250 FDP | 383 ± 170 |
| Con-A plus 1:500 FDP | 3592 ± 974 |
| Con-A plus 1:1000 FDP | 12288 ± 1880 |
| Con-A plus 1:10,000 FDP | 19046 ± 3237 |

As shown in Table 2, FDP inhibited the ConA-induced activation and proliferation of T-cells in a dose dependent manner, as evidenced by the much lower levels of labelled thymidine which were incorporated into the newly synthesized DNA of the cells treated by both FDP and ConA, compared to cells treated by ConA alone. Linear regression analysis of the data demonstrated a strong correlation between increasing FDP concentrations, and increased suppression of lymphocyte activation (r=0.886, P<0.02).

As expected, cyclosporin A also inhibited T-cell activation and proliferation in these tests. However, as noted above, cyclosporin A is a powerful and dangerous immunosuppressant drug, and does not offer a safe and practical treatment for asthma sufferers.

Accordingly, these data indicate that FDP can help suppress the inflammatory process in asthma sufferers, by helping control and prevent activation of T-lymphocytes in bronchial mucosa.

EXAMPLE 4: INHIBITION OF IL-2 EXPRESSION IN T-CELLS

The Applicant also investigated the expression of cytokines by T-lymphocytes. Isolated lymphocytes were obtained from rats, and incubated with stimulation by ConA treatment, as described above; treated cells were pre-treated with FDP, as described above, while control cells were not treated with FDP. After 5 days of incubation, RNA was extracted from the lymphocytes, using RNA-stat60. The integrity of RNA samples was evaluated by use of agarose-formaldehyde gel electrophoresis, and its quantity was determined spectrophotometrically.

The RNA was transcribed into complementary DNA (cDNA), using a reverse transcriptase enzyme. 10 $\mu$l of solution containing 1 $\mu$g of total cellular RNA was heated at 65° C. for 10 min, and then chilled on ice. To this solution was added 10 $\mu$l of a mixture containing 2× reverse transcriptase buffer (100 mM Tris-HCl, pH 8.3, 150 mM KCl, 6 MM $MgCl_2$), 1 $\mu$g oligo(dT)12–18, 100 $\mu$g/ml of acetylated bovine serum albumin, 0.5 mM mixed deoxynucleotides (dNTP), 10 units of RNAasin, and 100 units of MMLV reverse transcriptase enzyme. The mixture was incubated for 45 min at 35° C., then chilled on ice.

The cDNA sequences for three specific interleukins (IL-1, IL-2, and IL-6) were then amplified, using polymerase chain reaction (PCR) techniques, using previously published sense and anti-sense primer sequences for rat IL-1, rat IL-2, and rat IL-6. 10 $\mu$l of CDNA was amplified by PCR in a total volume of 100 $\mu$l. The PCR mixture contained a final volume of 1× PCR buffer (10 mM Tris-HCl, pH 8.3, 50 mM KCl, 1.5 mM $MgCl_2$), 50 mM dNTP, 0.1 $\mu$M each of the 5' and 3' primers, and 2.5 units of *Thermophilus aquaticus* DNA polymerase (purchased from Promega). The reaction mixture was amplified for 30 cycles in an automatic DNA thermal cycler. Each cycle had 3 steps: the double-helical strands were separated (denatured) at 94° C. for 45 seconds, the primers were allowed to anneal to the strands for 60° C. for 45 seconds, and any annealed primers were extended by the DNA polymerase at 72° C. for 2 minutes. After 30 cycles, an additional primer extension step was performed at 72° C. for 7 minutes.

20 $\mu$l of each PCR reaction product was electrophoresed on a 1.8% agarose gel in 0.5× Tris-borate-EDTA buffer. DNA bands, visualized by ethidium bromide staining and ultraviolet transillumination, were photographed with positive/negative 665-type film, and the photographic plates (negatives) were scanned by a densitometer.

The results of these tests on rat lymphocytes indicated that FDP-treated cells showed no detectable levels of RNA encoding the IL-2 protein, despite ConA stimulation. By contrast, control cells which did not receive FDP treatment showed substantial levels of RNA which encoded the IL-2 protein.

In addition, the amounts of IL-2 released by human T-cells were also evaluated, using ConA stimulation in the presence or absence of FDP. These tests used a commercially available human immunoassay kit (Inter Test-2X IL-2 Elisa Kit, sold by Genzyme Corp., Cambridge, Mass.) which uses monoclonal antibodies that bind specifically to human IL-2. The results, in Table 3, indicate that FDP, at all tested concentrations, abolished IL-2 production by the stimulated human T-lymphocytes. IL-2 concentrations are expressed in picograms per milliliter of media. Even despite activation by ConA, there was no detectable IL-2 in any of the FDP-treated human cell populations.

TABLE 3

FDP SUPPRESSION OF INTERLEUKIN-2 PRODUCTION
BY HUMAN T-CELLS STIMULATED BY CON-A

| Cell Treatment | After 24 Hours | After 72 Hours |
|---|---|---|
| Media only | ND | ND |
| Media + ConA (10 μg) | 916 ± 112 | 958 ± 62.9 |
| Media + ConA + FDP (1:100) | ND | ND |
| Media + ConA + FDP (1:500) | ND | ND |
| Media + ConA + FDP (1:1000) | ND | ND |

(ND = not detectable by ELISA assay)

EXAMPLE 5: EFFECTS OF FDP ON ACUTE EXPERIMENTAL ASTHMA INDUCED IN DOGS BY METHACHOLINE

Several different approaches have been used to study pulmonary gas exchanges during asthma-like attacks in lab animals. One such animal model involves bronchospasms which can be experimentally induced, in dogs, by inhalation of a drug called methacholine.

To carry out these tests, healthy mongrel dogs weighing 19 to 22 kg were anesthetized with sodium pentobarbital, 30 mg/kg IV, and intubated with endotracheal tubes. Initially, the ventilation was maintained with a Harvard ventilator, which served also to deliver methacholine, with or without aerosolized FDP. Subsequently, the animals were continuously ventilated prior to and following drug administration. Arterial venous and pulmonary artery (Swan-Ganz) were inserted, and used to obtain blood samples, monitor vascular pressures and measure cardiac output using thermodilution method. Arterial end pulmonary pressure, electrocardiogram, were constantly monitored on a DR-8 multichannel recorder. Arterial blood, hemoglobin, pH, $PO_2$, $PCO_2$, and potassium were measured with Radiometer ABL-4 (Copenhagen).

Upon completion of the surgical preparation, the dogs were allowed 30 min to stabilize hemodynamically. Several arterial blood samples were obtained and ventilation was adjusted so that arterial blood gases and pH were within physiologic range.

The bronchial challenge procedure entailed a 90 sec administration of aerosolized 0.5% methacholine hydrochloride (Sigma). In treatment animals, FDP (10% w/v) was administered for 3 minutes, in the same manner. Aerosols were delivered via Harvard respirator and microembulizer.

Blood gas measurements were made at 5, 15, and 30 minutes after drug inhalation was completed. Bronchoprovocation was either with methacholine alone (n=7), or following pretreatment with FDP (n=7).

All seven dogs treated with methacholine but not FDP suffered bronchospasm attacks. These attacks were accompanied by a significant decrease in blood pressure during methacholine administration, and there was also significant decrease in $PaO_2$ (mean and SEM $PaO_2$ values after 5 minutes were 47±2.85 mm Hg). These reductions in $PaO_2$ levels lasted for more than 30 minutes. Hemodynamic responses were more highly varied, but all dogs treated with methacholine but not FDP suffered from various levels of hemodynamic disruption.

By contrast, pretreatment with FDP resulted in smaller declines and disruptions in $PaO_2$ values. Mean $PaO_2$ values after 5 minutes were 70±5.62 mm Hg, and by 30 minutes after methacholine administration, $PaO_2$ values had returned to their normal baseline levels.

These data are shown in Table 4. Differences between FDP-treated and control dogs were compared by the two-tailed student's unpaired 't' test, and probability levels lower than 5% were considered to be significant.

TABLE 4

ARTERIAL BLOOD OXYGEN PARTIAL PRESSURE IN DOGS,
BEFORE AND AFTER METHACHOLINE INHALATION

| | Baseline | 5 min | 15 min | 30 min |
|---|---|---|---|---|
| Controls (no FDP) | 99 ± 5.74 | 47 ± 2.85 | 53 ± 3.86 | 62 ± 6.2 |
| Pre-treated with FDP | 89 ± 1.74 | 69 ± 6.49 (p = 0.007) | 81 ± 3.36 (p < 0.001) | 89 ± 3.16 (p = 0.002) |

In addition, five dogs were treated with FDP after (but not before) the administration of methylcholine. The $PaO_2$ levels in these dogs dropped to 64±4.26 mm Hg, 72±1.84 mm Hg, and 80±4.04 mm Hg, when measured at 5, 15 and 30 minutes (respectively) after FDP treatment. These $PaO_2$ levels were substantially higher and better than the $PaO_2$ levels of dogs that received only methylcholine (p<0.006, p<0.02 and p<0.01, respectively). There were no consistent alterations in $PCO_2$.

One animal was excluded from the data, since it developed a pulmonary embolism due to heart worms.

EXAMPLE 6: EFFECTS OF FDP ON LUNG FUNCTION IN HUMAN VOLUNTEERS

In five human volunteers (3 males, 2 females) who were generally healthy and who did not suffer from asthma, a 10% (w/v) solution of FDP in sterile water was inhaled for 5 consecutive breaths, using a standard MultiFit nebulizer (Misty OX, sold by the Medical Molding Corp. of America, Costa Mesa, Calif.) attached to a medical grade oxygen delivery system. When adjusted to deliver 56–68 L/min with a 5–6 L/min oxygen flow, the final oxygen content was 28%. The output tube from the nebulizer was connected to a standard face mask, which was placed on the face of the subject. The bottle of the nebulizer contained 100 ml of the FDP solution. The FDP dose delivered in the mist, during the 5 consecutive breaths, was calculated to be about 12 mg.

Prior to the FDP inhalation, in each volunteer, 3 consecutive peak expiratory flow rate (PEFR) measurements were made with the aid of an Astech Peak Flow Meter (Center Laboratories, Port Washington, N.Y. 11050). Briefly, these tests involved having each volunteer take as deep a breath as possible, and then blow as hard as possible into the meter. This was done over a period of a couple of minutes, giving the volunteer some time to catch his breath before and after each effort. The mean of these three measurements was considered as the baseline PEFR value for that person. Baseline heart rates, systolic and diastolic blood pressures, and body temperatures were also measured.

FDP inhalations (5 breaths in each set) were then made, approximately 15, 30, 45, 75, 105 and 165 minutes after the baseline measurements had been made. On several occasions, FDP inhalations were also made, 2 and 5 minutes after the baseline measurements were taken. After each such inhalation, three different expirations were measured, all within a couple of minutes after the FDP inhalation had been completed. The various measurements made after FDP inhalation were compared with the baseline values, before FDP administration. The t-test was used to compare paired observations, and differences were considered significant only when the two-tailed p value was <0.05.

The results showed that inhalation of 10% solution of FDP in aerosolized form caused significant increases in PEFR values, in all test subjects. The baseline PEFR value (before inhalation of FDP) was 471±29.6 L/min. Following FDP administration, the mean PEFR increased to 529±35.6 L/min (P<0.005). In addition, heartbeat rates declined significantly; baseline rates of 83.8±3.76 beats/min dropped after FDP treatment to 79.6±3.26 beats/min (P<0.025). Other measurements also indicated that FDP inhalation did not elicit any changes in blood pressure or body temperature.

There were fluctuations in the various measured PEFR values, but such fluctuations appeared to be what one would expect in a random sample drawn from a general population of normal subjects. PEFR values in the various different volunteers ranged from 353 to 565 L/min in baseline measurements, and from 378 to 645 L/min in post-treatment measurements.

One of the volunteers, at the end of the initial study, inhaled a 20% solution of FDP for 10 min on demand, using the same settings in the nebulizing delivery system. The calculated amount of FDP inhaled was 700 mg. After this inhalation session, his PEFR increased from a baseline value of 616 L/min, to 667 L/min. In a subsequent test on a different day, using a 10% FDP solution at a higher flow rate than for the earlier test, the same subject inhaled 750 mg of FDP over 10 minutes. A similar increase in PEFR was observed. No side effects were detected during either test.

On two occasions, the effects of albuterol sulfate inhalation solution (0.005% w/v in 0.9% NaCl) on PEFR was evaluated, using identical procedures. The albuterol sulfate did not induce any significant change in PEFR.

These tests were all done under the supervision of a trained physician, with informed consent from all participants. In all of these tests, no side effects were noticed by any of the volunteers, other than the above-noted decreases in heart rates and increases in pulmonary ventilation rates.

EXAMPLE 7: EFFECTS OF FDP ON BRONCHITIS WITH CHRONIC COUGHING

In the tests on human volunteers described in Example 6, one test subject had a chronic cough, which appeared to be secondary to allergic bronchitis. This subject participated in several studies over 10 days. Prior to FDP inhalation, her baseline PEFR was 390 L/min. This value increased with each and every FDP treatment. At 10 days after the first inhalation, the PEFR of this subject had increased to 520 L/min (P<0.01). Upon interrogation, she reported that her breathing was substantially improved, and her coughing had nearly disappeared.

This observation indicates that FDP, when administered in this manner, can exert a cumulative improvement in pulmonary ventilation, and in at least some patients, offers a useful treatment for bronchitis and chronic coughing, It is also anticipated that FDP is likely to provide some relief to people who suffer from emphysema, and possibly from other chronic pulmonary problems as well.

Thus, there has been shown and described a new and useful method for asthma. Although this invention has been exemplified for purposes of illustration and description by reference to certain specific embodiments, it will be apparent to those skilled in the art that various modifications, alterations, and equivalents of the illustrated examples are possible. Any such changes which derive directly from the teachings herein, and which do not depart from the spirit and scope of the invention, are deemed to be covered by this invention.

REFERENCES

Alexander, A. J., et al, "Cyclosporin A and corticoid-dependent severe asthma randomized double-blind placebo control crossover trial," *Lancet* 339: 324–328 (1992)

Barnes, N. C., "Current therapy for asthma: time for a change?" *J Pharm Pharmacol* 49 *Suppl.* 3: 13–16 (1997)

Bentley, A. M., et al, "Human late asthmatic reactions," *Clin Exp Allergy* 27 *Suppl* 1: 71–86 (1997)

Corrigan, C. J., et al, "T-cell/eosinophil interactions in the induction of asthma," *Eur Respir J Suppl* 22: 72s–78s (1996)

Everard, M. L., "Management of asthma in childhood," *J Pharm Pharmacol* 49 *Suppl* 3: 45–50 (1997)

Floreani, A. A., et al, "Experimental treatments for asthma," *Curr Opin Pulm Med* 3: 30–41 (1997)

Fukuda, T., et al, "Cyclosporine A reduces T lymphocyte activity and improves airway hyperresponsiveness in corticosteroid-dependent chronic severe asthma," *Ann Allergy Asthma Immunol* 75: 65–72 (1995)

Higgs, O. A., "Novel approaches to the inhibition of cytokine responses in asthma," *J Pharm Pharmacol* 49 *Suppl* 3: 25–31 (1997)

Jacoby, D. B., "Role of the respiratory epithelium in asthma," *Res Immunol* 148: 48–58 (1997)

Markov A K, et al., "FDP: An agent for treatment of experimental endotoxin shock," *Surgery* 90: 482–8 (1981)

Nourshargh, S., "Adhesion molecules and asthma," *J Pharm Pharmacol* 49 *Suppl* 3: 33–8 (1997)

Saint-Remy, J. M., "Modulation of anti-allergen immune responses by allergen-antibody complexes," *Adv Exp Med Biol* 409: 417–24 (1996)

Spector, S. L., "Alternative treatments in the patient with intractable asthma," *Curr Opin Pulm Med* 3: 23–9 (1997)

Virchow, J. C., et al, "T cells and cytokines in broncho-alveolar lavage fluid after segmental allergen provocation in atopic asthma," *Am. J. Respir. Crit. Care Med.* 151: 960–8 (1995)

I claim:

1. A method of treating an asthma attack in a human patient, comprising the step of inhaling into the bronchial passageways and lungs an inhalable formulation containing fructose-1,6-diphosphate.

2. The method of claim 1, wherein the inhalable formulation contains fructose-1,6-diphosphate dissolved in an aqueous solution.

3. The method of claim 2, wherein the inhalable formulation contains fructose-1,6-diphosphate at a concentration between about 5% and about 40%, expressed as weight per volume.

4. The method of claim 2, wherein the inhalable formulation is an aerosol.

5. The method of claim 2, wherein the aqueous solution containing fructose-1,6-diphosphate is passed through a nebulizer prior to inhalation.

6. A method of treating an asthma attack in a human patient, comprising the step of intravenously injecting into the patient an injectable formulation containing fructose-1,6-diphosphate.

7. The method of claim 6, wherein the injectable formulation contains fructose-1,6-diphosphate dissolved in an aqueous solution.

8. The method of claim 7, wherein the injectable formulation contains fructose-1,6-diphosphate at a concentration between about 5% and about 40%, expressed as weight per volume.

9. An article of manufacture, comprising an inhaler device and a fluidized substance contained therein, wherein the inhaler device is designed for use by humans suffering from asthma attacks, and wherein the fluidized substance contains fructose-1,6-diphosphate in a formulation that is intended for inhalation directly into human bronchial passageways.

10. The article of manufacture of claim 9, wherein the inhalable formulation contains fructose-1,6-diphosphate dissolved in an aqueous solution.

11. The article of manufacture of claim 10, wherein the inhalable formulation contains fructose-1,6-diphosphate at a concentration between about 5% and about 40%, expressed as weight per volume.

* * * * *